United States Patent
Diamant et al.

(10) Patent No.: US 9,743,980 B2
(45) Date of Patent: Aug. 29, 2017

(54) METHOD AND SYSTEM FOR ASSISTING A WIRE GUIDE TO CROSS OCCLUDED DUCTS

(75) Inventors: Valery Diamant, Katzrin (IL); Vladimir Chernenko, Tomsk (RU); Marat Lerner, Tomsk (RU); Ludmila Ivanova, Tomsk (RU); Alexey Dutov, Tomsk (RU); Nadezda Yasko, Tomsk (RU)

(73) Assignee: Safepass Vascular Ltd (IL)

( * ) Notice: Subject to any disclaimer, the term of this patent is extended or adjusted under 35 U.S.C. 154(b) by 1616 days.

(21) Appl. No.: 12/711,755

(22) Filed: Feb. 24, 2010

(65) Prior Publication Data

US 2011/0208185 A1    Aug. 25, 2011

(51) Int. Cl.
| | |
|---|---|
| *A61B 18/14* | (2006.01) |
| *A61B 17/22* | (2006.01) |
| *A61B 18/00* | (2006.01) |
| *A61B 18/16* | (2006.01) |

(52) U.S. Cl.
CPC .......... *A61B 18/1492* (2013.01); *A61B 18/14* (2013.01); *A61B 2017/22038* (2013.01); *A61B 2017/22094* (2013.01); *A61B 2018/00178* (2013.01); *A61B 2018/00422* (2013.01); *A61B 2018/00547* (2013.01); *A61B 2018/00577* (2013.01); *A61B 2018/162* (2013.01)

(58) Field of Classification Search
CPC A61B 2018/00178; A61B 2018/00422; A61B 2018/00547; A61B 2018/00577; A61B 2018/162; A61B 18/14; A61B 18/1492; A61B 2017/22038; A61B 2017/22094

USPC ................................................ 606/41, 45–50
See application file for complete search history.

(56) References Cited

U.S. PATENT DOCUMENTS

| | | |
|---|---|---|
| 2,559,227 A | 7/1951 | Rieber |
| 3,982,541 A | 9/1976 | L'Esperance, Jr. |
| 4,308,905 A | 1/1982 | Gallagher |
| 4,605,003 A | 8/1986 | Oinuma et al. |
| 4,654,024 A | 3/1987 | Crittenden et al. |
| 4,722,340 A | 2/1988 | Takayama et al. |
| 4,927,427 A | 5/1990 | Kriauciunas et al. |

(Continued)

FOREIGN PATENT DOCUMENTS

| | | |
|---|---|---|
| CA | 2104414 A1 | 2/1995 |
| DE | 3633527 A1 | 4/1988 |

(Continued)

OTHER PUBLICATIONS

The AUTOLITH Lithotriptor, Nortech Advanced Technology for Better Medicine, Lithotripsy Products, 1999 Northgate Technologies, Inc., 2 pgs.

(Continued)

*Primary Examiner* — Michael Peffley
*Assistant Examiner* — Samantha Good
(74) *Attorney, Agent, or Firm* — Blank Rome LLP

(57) ABSTRACT

A method and a system for assisting a wire guide to cross obstructed ducts in mammalian body are described. The method and system is based on applying pulsed energy to occlusion obstructing the duct. The pulsed energy is applied by means of an auxiliary probe. The auxiliary probe is relatively displaceable with respect to the wire guide along a lumen provided within the probe. The distal region of the probe is provided with enhanced flexibility comparing with the reminder portion of the probe.

14 Claims, 10 Drawing Sheets

(56) References Cited

U.S. PATENT DOCUMENTS

| | | |
|---|---|---|
| 5,009,656 A | 4/1991 | Reimels |
| 5,254,121 A | 10/1993 | Manevitz et al. |
| 5,350,375 A | 9/1994 | Deckelbaum et al. |
| 5,419,767 A | 5/1995 | Eggers et al. |
| 5,448,363 A | 9/1995 | Hager |
| 5,722,980 A | 3/1998 | Schulz et al. |
| 6,007,514 A | 12/1999 | Nita |
| 6,149,656 A | 11/2000 | Walz et al. |
| 6,261,298 B1 | 7/2001 | Irion et al. |
| 6,319,261 B1 | 11/2001 | Bowers |
| 7,087,061 B2 | 8/2006 | Chernenko et al. |
| 2008/0015570 A1 | 1/2008 | Ormsby et al. |
| 2008/0147170 A1 | 6/2008 | Vrba |
| 2008/0172067 A1 | 7/2008 | Nita et al. |
| 2008/0294162 A1 | 11/2008 | Rossetto et al. |
| 2009/0171278 A1 | 7/2009 | Hirszowicz et al. |
| 2009/0192405 A1 | 7/2009 | Carney |
| 2009/0209900 A1 | 8/2009 | Carmeli et al. |

FOREIGN PATENT DOCUMENTS

| | | |
|---|---|---|
| DE | 3927260 A1 | 2/1991 |
| DE | 19609019 A1 | 9/1997 |
| DE | 19810696 C1 | 5/1999 |
| WO | 9710058 A1 | 3/1997 |
| WO | 03075777 A1 | 9/2003 |
| WO | 2007095498 A1 | 5/2007 |
| WO | 2008035349 A1 | 2/2008 |
| WO | 2008102346 A1 | 5/2008 |

OTHER PUBLICATIONS

B.V. Semkin, A.F. Usov, V.I. Kurets, The Principles of Electric Impulse Destruction of Materials, Russian Academy of Sciences, 1993, 1995, Saint-Petersburg, Nauka, 8 pgs, (English translation of passages marked).

European Search Report with Abstract and Description for co-pending application EP 11150665.5 dated Jun. 1, 2011.

Regularity of Solid Dielectric Breakdown at the Interface with Liquid Dielectric Under Action of Voltage Pulse, Russian Academy of Sciences, International Association of Scientific Discoveries Authors, Diploma No. 107 for the discovery, 3 pgs, English translation 2 pgs, Apr. 29, 1988.

METHOD AND SYSTEM FOR ASSISTING A WIRE GUIDE TO CROSS OCCLUDED DUCTS

FIELD OF THE INVENTION

The present invention relates to medicine, namely to medical devices for performing medical treatment procedures in ducts of mammalian body. More particularly the invention refers to medical devices for performing intrusive endoluminal procedures inside hollow organs or cavities in a human body, e.g. coronary stenting, intravascular percutaneous coronary interventions or other procedures. For performing such procedures are used stents, balloons or other medical devices delivered within the duct with the aim of so-called wire guide deployed endoluminally before introducing the medical device. The wire guide is a wire that is inserted into lumen to guide a medical device, e.g. catheter to a certain location in the body where the endoluminal treatment is to be performed. Upon deployment the wire guide a medical device e.g. a balloon dilatation catheter is passed over the wire guide to the required location.

Unfortunately when the lumen is occluded or has significant curvature it is not always possible to advance the wire guide as distally as desired to reach the required location.

The present invention addresses to this problem and refers to a dedicated probe which efficiently assists to advance the wire guide through an occluded lumen, like hollow organ, cavity, duct or vessel irrespective whether it is rectilinear or curvilinear.

For the sake of brevity in the following description the hollow organs, cavities or vessels will be referred-to simply as ducts.

Even more particular the present invention refers to a probe which is capable to at least partially disrupt the occlusion by means of electro-impulse method and to render crossing the duct by the wire guide easier. Among various obstructions, which can be at least partially disrupted by the probe of the present invention are first of all stones, e. g. gallstones, kidney stones, cystine stones and other calculi, appearing in biliary, urinary or coronary system, peripheral vasculature of the lower extremities or other system of human body.

For the sake of brevity the various formations, calculi or other obstructions as might occur in the duct of a mammalian body will be referred-to further simply as occlusions.

It should be understood however that the present invention is not limited to disrupting of occlusions appearing merely in a human body. It can be employed during medical treatment of animals as well.

Furthermore the present invention is not limited to disrupting of above-mentioned occlusions which are of inorganic nature. It is also suitable for destroying of occlusions of organic nature which might occlude any kind of ducts of mammalian body. Some non-limited examples of such organic occlusions comprise abnormal tissue causing arrhythmia, human atherosclerotic plaque, tromboembolic obstruction, chronic total occlusion (CTO), etc.

BACKGROUND OF THE INVENTION

There are known in the art various solutions devised for assisting the wire guide to cross a duct in human body.

So for example in US 2009209900 there is disclosed device and method for opening vascular obstructions. According to this method there is provided a catheter tube capable of inducing vibrations in a wire guide itself. The vibrations are induced by a magnetic field actuating means.

In U.S. Pat. No. 6,007,514 there is described ultrasonic system with path finding wire guide. The system comprises a wire guide coupled to an ultrasonic catheter which is capable of transmitting ultrasonic energy directly to occlusions.

In US 2008172067 there is described steerable ultrasonic catheter which is provided with ultrasound transmission members with increased distal flexibility allowing contact between the wire guide and ultrasonic catheter.

In WO 2008102346 there is described a wire guide system in which the distal portion is bendable ex vivo to introduce and navigate the distal portion into the vasculature of a specific body and while in vivo.

In US 2009192405 there is described intraluminal guidance system using bioelectric impedance to guide elongate transluminal device through an occlusion in a vessel. The system comprises a couple of electrodes to which an electric current is supplied and a voltage drop between the electrodes is measured. One of the electrodes is located on a distal portion of the transluminal device and the second electrode is in electric contact with the patient. The voltage drop is converted into bioelectric impedance and based on its measurement it is possible to determine if the transluminal device is approaching the vessel wall thus permitting to redirect the device away from the vessel wall.

In US 2008147170 there is disclosed medical device for crossing an occlusion in a vessel. The medical device such as a wire guide is provided with plurality of angled slots to increase the lateral flexibility during navigation of the wire guide.

In WO 2008035349 there is disclosed device and method for crossing a vascular occlusion. The device comprises a catheter and a wire guide insertable through the catheter. A hydraulic chamber is provided between the catheter and the occlusion with the liquid therein having an elevated pressure sufficient for creating a pathway for the wire guide.

In WO 2007095498 there is described a wire guide provided with a shaft and with a stylet deployed in a lumen of the shaft such that the stylet is selectively actuatable within the shaft.

In U.S. Pat. No. 4,654,024 there is disclosed a catheter with a heater mounted on its distal end for melting atherosclerotic plaque to clear an obstruction within an artery. A wire guide is inserted into the lumen of the catheter and the catheter is directed into the proper coronary branch by means of the wire guide. The wire guide is advanced until it meets the obstruction. The heater is then operated and the catheter is advanced as the plaque melts. Once a suitable channel has been opened, the catheter is removed and a conventional balloon dilatation catheter is slid over the wire guide.

In U.S. Pat. No. 5,350,375 there is disclosed a catheter with laser induced fluorescence intensity feedback and control during laser angioplasty. The catheter includes an eccentric wire guide lumen and at least one optical fiber positioned relative to an obstruction in a blood vessel with possibility for rotating the catheter and monitoring the fluorescence intensity. When the fluorescence intensity has a maximum value, the optical fiber is aligned with the obstruction. The fluorescence intensity feedback is used to determine when a laser ablation device has crossed an occlusion. An abrupt drop in fluorescence intensity indicates that the ablation device has crossed the occlusion.

The known in the art solutions may be arbitrary divided into two main groups.

The first group includes solutions intended merely for assisting the crossing of obstructed duct by improving flexibility of the wire guide without however disrupting the obstruction occurred in the duct.

The second group includes solutions intended for disruption by applying energy to the obstruction while the energy is induced either in the wire guide itself or in an auxiliary catheter or probe accompanying the wire guide during its advancement along the duct. Among those methods one can mention ultra-sound, hydraulic, laser, and other methods.

On the other hand there are known in the art medical lithotriptors which operation is based on so-called electro-impulse principle.

This principle was adopted from mining technology, where it has been used for so-called high-power electro-impulse destruction of materials. This principle is based on applying of electrical impulses with the rise time of not more than 500 nanoseconds to two electrodes positioned on a solid mineral material immersed in dielectric liquid or liquid medium with relatively small conductivity. The applying of such impulses is associated with producing discharge, which does not propagate through the surrounding liquid medium, but rather through the bulk of the solid body itself.

The electro-impulse technology was developed in late fifties in Russia and since then it was successfully implemented in such fields like crushing and disintegration of hard rocks and ores in mining industry, destructing of concrete blocks in building industry, drilling of frozen ground and extremely hard rocks, crushing of various inorganic materials, etc.

A survey of this technology can be found in a monograph "Basics of electro-impulse destroying of materials", by Semkin et at. Saint-Petersburg, Nauka, 1993.

According to this technology two or more electrodes are placed immediate on the surface of a solid body (rock) and very short impulses of voltage U (t) are sent through them. Once an electrical breakdown between the electrodes is initiated, it occurs in the bulk of the solid body and is associated with producing of the breakdown discharge channel that extends within the bulk of the body.

The body itself serves as a medium to promote propagation of the electrical breakdown rather than the surrounding medium. Extension of the discharge channel through the body is accompanied by mechanical stresses, which stretch the body and destroy it as soon as tensile strength of the body is exceeded.

In fact in the process of electro-impulse destroying the initiation and propagation of the discharge is similar to a micro-explosion within the body.

It can be readily appreciated that since tensile strength of a rock is at least an order of magnitude less than its compressive strength, the electro-impulse crushing is associated with consumption of much less energy, than conventional electro-hydraulic crushing.

It has been also empirically established, that the probability of propagation of the breakdown channel through the body is higher when a very short voltage impulses are applied to electrodes, positioned on a solid body immersed in a liquid medium, since the voltage required for the breakdown within the bulk of the body is less, than the voltage required for breakdown within the liquid medium outside of the body.

Despite the fact that this technology exists for more than 40 years it has been employed mainly in mining and building industry for destruction of very large objects like rocks or concrete blocks as e.g. disclosed in International publication WO 9710058.

The electro-impulse technology was only recently employed in medicine for lithotripsy treatment of calculi and a lithotriptor implementing this technology has been devised. This lithotriptor is manufactured by the company Lithotech Medical Ltd., Israel and is commercially available for urology procedures, under the name "Urolit". The method and apparatus for electro-impulse lithotripsy is disclosed in International application PCT/IL03/00191.

Thus one can conclude that the problem of passing a wire guide through an occluded duct is known for a long time and there exist many attempts to solve it. Nevertheless there is still a room for a new solution. This new solution could beneficially combine advantages of electro-impulse disrupting along with imparting to auxiliary catheter high flexibility and maneuverability during advancement thereof through occluded duct.

OBJECTS OF THE INVENTION

The main object of the present invention is to provide a new and improved method and system for assisting a wire guide to cross an occluded duct in mammalian body which reduces sufficiently or overcomes the drawbacks of the known in the art solutions.

In particular the first object of the invention is to provide a new and improved method and system for assisting a wire guide to cross an occluded duct by supply of pulsed energy to an auxiliary probe which working head is brought in contact with an occlusion in the duct to at least partially disrupt the occlusion.

By at least partially disrupting here is meant causing such minimal damage to the occlusion, which is sufficient to allow the wire guide to pass the occlusion. For a mineral occlusion, e.g. CTO, it could be just cracking.

Still further object of the invention is to provide a new and improved method and system for assisting a wire guide to cross an occluded duct by at least partial disrupting the occlusion by supplying pulses of energy to the occlusion.

Another object of the invention is to provide new and improved method and system for assisting a wire guide to cross an occluded duct irrespective of the type of the occlusion, i.e. irrespective of whether the occlusion is of organic or inorganic nature.

A still further object of the invention is to provide a new and improved system for assisting a wire guide to cross an occluded duct of a mammalian body when the duct is a peripheral or coronary vessel occluded by a chronic total occlusion (CTO).

A still further object is to provide a new and improved system suitable for assisting a wire guide to cross an occluded duct irrespective of the type of the duct or organ, i.e. whether it is a blood vessel, coronary vessel, urinary tract, biliary tract, intestine, or prostate.

Yet another object of the invention is to provide a new and improved system for assisting a wire guide to cross an occluded duct by virtue of a probe, the flexibility and maneuverability of which are sufficient for reliable advancement along a straight or curved occluded duct.

A still further object of the invention is to provide a new and improved system for assisting a wire guide to cross an occluded duct, which is not harmful for tissues of the mammalian body.

Yet another object of the invention is to provide a new and improved system for assisting a wire guide to cross an occluded duct of a mammalian body, which allows bringing an auxiliary catheter to the occluded location by sliding the catheter over the wire guide either according to the Monorail® principle or another principle.

Another object of the invention is to provide a new and improved system for assisting a wire guide to cross an occluded duct of a mammalian body by virtue of a probe having a working head, the location of which can be tracked during advancement along the duct.

The above and other objects and advantages of the present invention can be achieved in accordance with the following combination of its essential features, referring to different embodiments thereof as a system for assisting a wire guide to cross an occluded duct of a mammalian body.

As an example for use with a system according to the invention, a method is provided for assisting a wire guide to cross an occlusion obstructing a duct of a mammalian body, said method comprising:

a) Providing a probe insertable into the duct, said probe having a working head, said probe being electrically connectable to a control unit, said probe having a lumen for receiving the wire guide and said probe having at least one opening for introducing the wire guide in the lumen, b) Protracting the wire guide through the lumen along the duct until it approaches the occlusion, c) Displacing the probe relatively to the wire guide to bring the working head in physical contact with the occlusion, d) Supplying pulses of energy from the control unit to the working head to at least partially disrupt the occlusion and render further advancement of the probe along the duct possible, e) Displacing the wire guide relatively to the probe along the duct towards a required location.

According to one embodiment said pulses of energy can be defined by the following parameters: duration not more then 5000 nanoseconds, pulse rise time less than 50 nanoseconds, pulse energy 0.01-1 Joule and pulse amplitude 3-15 kV.

According to further embodiment said pulses can be either one time discrete pulses or series of pulses.

As per still further embodiment the method comprises detachable electrical connecting the probe and the control unit.

Yet another embodiment comprises setting parameters of the pulses before supplying them to the probe.

According to other embodiment said occlusion can be selected from the group consisting of organic occlusions, inorganic occlusions and their combination.

In yet further embodiment said duct can be selected from the group consisting of a hollow organ, a cavity and a vessel.

In still further embodiment said occlusion can be Chronic Total Occlusion (CTO).

According to another embodiment said pulses of energy can be defined by the following parameters: duration not more then 5000 nanoseconds, pulse rise time less than 50 nanoseconds, pulse energy 0.01-0.3 Joule and the pulse amplitude which is sufficient for stable discharge breakdown between two electrodes on the distal end of the probe's head. Taking into account the electric strength of materials used for manufacturing the probe, as well as the distance between two electrodes, which is about 0.1 mm the value of the pulse amplitude can be 3-7 kV and amount of pulses can be 60-600.

And in yet another embodiment said displacement of the wire guide can be carried out according to Monorail® principle.

According to the aspect of the invention referring to a system for assisting a wire guide to cross a duct in a mammalian body when the duct is obstructed by an occlusion, said system being suitable to at least partially to disrupt the occlusion by supplying pulses of energy to the occlusion, said system comprising:

an auxiliary probe insertable in the duct, said auxiliary probe is configured with elongate body portion having a distal end and a proximal end, said probe having a working head fitted with a potential electrode and with a ground electrode, said working head is coupled to the distal end and said auxiliary probe having a lumen longitudinally extending through at least a fraction of the body portion and through the working head;

a control unit for generation and controlling pulses of energy to be supplied to electrodes of the working head;

a power cable for electrical connection the auxiliary probe to the control unit;

wherein the lumen is provided with at least one opening for introducing the wire guide therethrough to allow relative displacement between the wire guide and the auxiliary probe along the lumen, and the body portion comprises a region, which is disposed adjacent the working head, said region having enhanced flexibility comparing to a reminder of the body portion.

According to one embodiment of the system said auxiliary probe can be provided with a miniature coaxial cable having an inner electrode and a shield electrode, said miniature coaxial cable being received within a lumen extending along the body portion between the proximal end thereof and the region having enhanced flexibility.

According to other embodiment said control unit can be capable to supply pulses defined by the following parameters: duration not more then 5000 nanoseconds, pulse rise time less than 50 nanoseconds, pulse energy 0.01-1.0 Joule and the pulse amplitude which is sufficient for creation stable discharge breakdown between two electrodes on the distal end of the probe's head. This pulse amplitude may be 3-15 kV.

In a still further embodiment a coupler can be provided with a male portion associated with the probe and with a female portion associated with the power cable.

In another embodiment said power cable can be a high voltage coaxial cable having a core electrode and a shield electrode, wherein the core electrode is electrically connected with the inner electrode of the miniature coaxial cable and the shield electrode of the power cable is electrically connected with the shield electrode of the microcable.

As per a still further embodiment the inner electrode of the miniature coaxial cable can be electrically connected with the potential electrode of the working head while the shield electrode of the microcable can be electrically connected with the ground electrode of the working head.

In another embodiment the potential electrode and the ground electrode of the working head can be configured as respective outer and inner cylindrical bushings.

In other embodiment a distal end of the ground electrode is not flush with a distal end of the potential electrode and the ground electrode can be buried within the working head with respect to the potential electrode.

According to yet another embodiment the probe can be provided with an outside cover and with at least one reinforcing element affixed to an inwardly facing surface of the outside cover.

As per a further embodiment the lumen for receiving the wire guide can comprise a plastic tube and the lumen for receiving the microcable can comprise a stainless steel coil.

In an alternative embodiment both the lumen for receiving the wire guide and the lumen for receiving the microcable can be made from a stainless steel coil.

According to other embodiment the shield electrode of the microcable can be electrically connected to the lumen for receiving the wire guide.

According to another embodiment the probe can be provided with an additional grounding electrode, which is electrically connected with the shield electrode of the power cable and to the lumen for receiving the wire guide.

As per further embodiment the probe can be provided with an intermediate member for coupling between the region of enhanced flexibility and a reminder portion of the probe and the intermediate member can be configured as a muff made of polyurethane.

According to another embodiment, the probe can be provided with a centering means which is suitable to keep the distal end of the probe directed along the lumen and to prevent bending of the probe due its sliding along an occlusion which has slanted wall.

The present invention has only been summarized briefly. For better understanding of the present invention as well of its embodiments and advantages, reference will now be made to the following description with reference to the accompanying drawings.

DETAILED DESCRIPTION OF THE INVENTION

Figure 1:
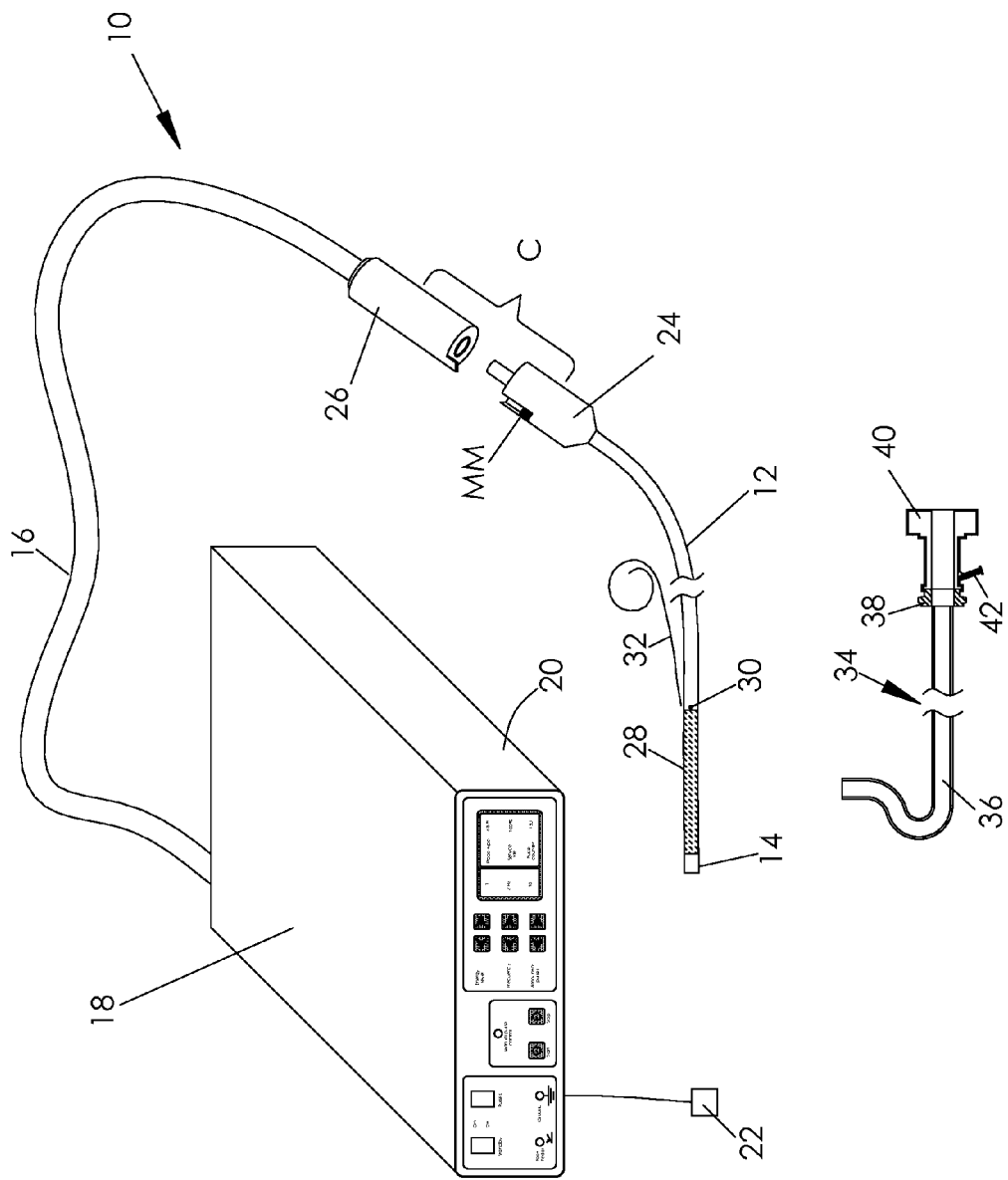
FIG. 1 shows general view of a system for assisting a wire guide to cross a duct in a mammalian body.

With reference to FIG. 1 an embodiment of the system of the invention is shown. This embodiment and the further embodiments refer to the system operating according to electro-impulse principle mentioned above and described for example in PCT/IL03/00191. It should be borne in mind however that the present invention can be implemented also in other systems which employ pulsed energy for at least partial disrupting occlusions in ducts of mammalian body.

In FIG. 1 is seen a system 10 comprising a flexible probe 12 having a distal and a proximal end.

In the further disclosure the term distal refers to a direction towards occluded location within the duct while the term proximal refers to an opposite direction.

At the distal end of the probe a probe working head 14 is fitted.

In practice the length of the probe is 1400-1500 mm and outside diameter 2-4 Fr. The working head has length of about 5 mm.

Before initiating treatment session the probe head is inserted into a duct where the occlusion to be destroyed is located and a forwardmost end of the working head is brought in physical contact with the occlusion. The proximal end of probe is detachably connectable to a power cable 16, which in its turn is electrically connected to a control unit 18 from which pulsed electrical energy is delivered to the probe head. The control unit is provided with a housing 20 accommodating those components which are necessary for generating electrical pulses defined by electrical parameters suitable for efficient disrupting the occlusion. When the probe is connected to the cable it is possible to deliver pulsed energy from the control unit to the probe's working head.

In practice when the system operates according to the electro-impulse principle pulses of energy supplied to the probe's working head from the control unit are defined by duration time of not more than 5000 nanoseconds, impulse rise time less than 50 nanoseconds, impulse energy 0.01-1.0 joule and impulse amplitude 3-15 kV. The preferred configuration of impulses is rectangular and they can be supplied during disrupting session either discretely as one time impulses or as series of repeating pulses supplied with frequency of 1-5 Hz.

The control unit is provided with a foot pedal 22, electrically connected preferably to a front side of the control unit. By pressing on the pedal an operator can initiate generation of a pulse or one or more series of pulses and send the pulsed energy with the required parameters to the working head.

The probe is detachably connectable with the cable by a coupler C, which comprises a male portion 24 associated with the proximal end of the probe and a female portion 26 associated with the cable. In FIG. 1 the coupler is shown in disconnected state, i.e. the male portion is separated from the female portion. One can readily appreciate that for operation of the system the male portion of the coupler is inserted in the female portion to bring the coupler in connected state.

Since during the treatment session the probe's head wears the probe should be periodically replaced. Furthermore, some times it might be required to use probes with different diameters. By virtue of detachable connecting the control unit to the probe it is possible timely, conveniently, fast and easy to replace the probe.

At a front side of the control unit housing there are provided various indicators and knobs for setting the required parameters of the pulsed energy delivered to the probe. The above-mentioned indicators and knobs are described in our co-pending patent application U.S. Publication No. 2011/0208206, titled "Method and system for destroying of undesirable formations in mammalian body".

It is not seen in FIG. 1 but should be appreciated that at a rear side of the control unit housing there is provided an electric outlet for electrical connecting the control unit to a source of feeding voltage, a contact for grounding the control unit housing and a port for electrical connecting the control unit with cable 16.

In practice it would be preferable that when the probe is connected to the cable a power line establishes between the probe and the control unit and a signal line establishes between the probe and the control unit through which exchange of information might take place. The power line is implemented as a high voltage coaxial cable, having high voltage core electrode and shield electrode. The signal line can be implemented as a miniature coaxial cable.

Furthermore, it is preferable that the probe is provided with a memory means MM, which stores initially preset amount of pulses corresponding to remaining service life of the probe and/or information referring to conditions of previous disrupting treatments which have been carried out by the system. By virtue of this provision delivery of the pulsed energy to the probe in the course of a new disrupting session can be controlled such that the system is terminated as soon as remaining service life of the probe approaches certain preset limit. In this situation operator is alarmed that the probe is worn and it should be replaced by a fresh one. By providing possibility for timely replacement of the probe efficient and safe operation of the system is preserved.

Within the control unit are deployed various electronic and electric components, which enable inter alia generation of pulses, control of parameters of pulses, monitoring of remaining service life of the probe, calculating new value of remaining service life and its updating in the memory means. The housing of the control unit should be provided with grounding which status can be automatically checked before initiation of a treatment session. The control unit can be also provided with an alarm, which advises an operator when the remaining service life approaches a certain preset value.

The above-mentioned features are described in our co-pending patent application, U.S. Publication No. 2011/0208206, titled "Method and system for destroying of undesirable formations in mammalian body".

Another embodiment of the system fitted with the memory means is also possible. In this embodiment instead of a miniature coaxial cable for the signal line a wireless link can be used for establishing a signal line between the probe and the control unit. This link can be implemented by providing both the male portion 24 of the coupler and the control unit 18 with respective transceivers, which would communicate by sending and receiving respective signals. As a suitable transceiver one can use a programmable RFID tag programmed with identification information referring to the probe, e.g. its diameter, the current value of the remaining service life and other identification information. The transceiver installed in the control unit can be an appropriate interrogator/reader capable to communicate with the RFID tag. The wireless communication link may include any type of link, e.g. infra-red, radiowave or microwave wireless communication link.

One should readily appreciate that in the case of wireless communication between the probe and the control unit the cable 16 constitutes merely a power line through which pulsed energy is delivered from the control unit to the probe.

It is also schematically shown in FIG. 1 that near the working head of the probe 12 a distal region 28 is provided, which is defined by enhanced flexibility. In practice the length of the region of enhanced flexibility is about 50-200 mm.

It is also schematically depicted that the probe is provided with a lateral opening 30 through which a wire guide 32 can be withdrawn from a dedicated lumen within the probe as will be described in details later on. The location of the opening as shown in FIG. 1 is suitable for relative displacement of the probe and the wire guide according to the Monorail® principle. The proximal end of the probe can be provided with a port for withdrawing the wire guide so as to enable relative displacement of the probe and the wire guide according to the Over-the-wire principle.

The wire guide is entered in the probe and protracted along the duct in order to provide a safely access of the probe to a desired location where a medical treatment should be carried out.

The wire guide has an outside diameter of 0.34 mm.

The probe 12 is used as an auxiliary means in a situation when the duct is occluded to assists the wire guide to cross the occlusion. One should appreciate however that once the wire guide has accessed the required location within the duct, the auxiliary probe 12 is evacuated from the body and replaced by a medical device, e.g. coronary stent, balloon dilatation catheter or other treatment catheter which can be passed over the wire guide into the duct.

The region of enhanced flexibility extends between working head 14 and lateral opening 30 and in practice its length is 5-15 cm depending on the probe's diameter and its length.

By virtue of this provision the probe has improved maneuverability rendering relative displacement of the probe and the wire guide along the duct easier.

In FIG. 1 is also depicted a guiding catheter 34 through which auxiliary probe 12 is introduced in the duct of mammalian body. The guiding catheter is known per se and does not constitute a part of the system 10. The guiding catheter is provided with a hollow shaft 36 having inside diameter which is sufficient for passing the auxiliary probe 12. In practice this diameter lies in the range of 6-8 Fr. Proximal end of the shaft is connected via an adapter 38 to a Y-connector 40. The Y-connector is fitted with a port 42, which can be used either for delivery a contrast fluid or an irrigating fluid or for suction or for any other purpose.

Referring now to FIGS. 2a-2f it will be explained a method for assisting the wire guide to cross an occluded duct.

Figure 2:
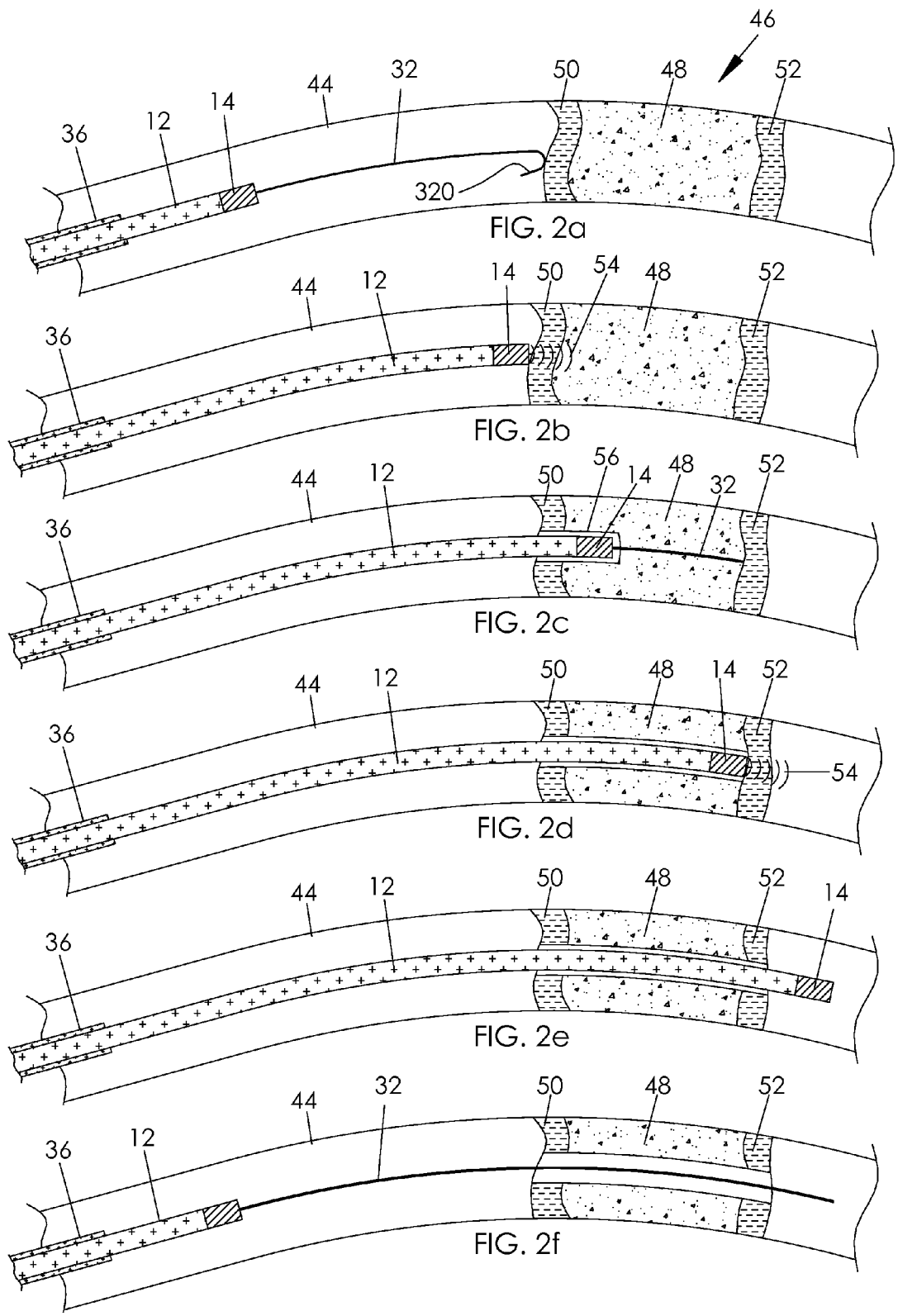
FIG. 2 illustrates an example of a method for assisting a wire guide to cross a duct in a mammalian body when the duct is obstructed by an occlusion.

In FIG. 2a is shown probe 12 after it has been introduced through guiding catheter 34 within a curvilinear duct 44 of mammalian body, e.g. a coronary artery or other vessel. Wire guide 32 is protracted from the distal region towards an occlusion 46 located within the duct and obstructing further advancement of the wire guide such that a forward end 320 wire guide bends and can't be advanced any more. The occlusion can be for example chronic total occlusion (CTO), which is schematically shown as consisting of a relatively soft core region 48 confined between more hard boundary regions 50, 52. The core region might consist of an organic tissue, while the boundary regions might consist of mineral, e.g. calcified material.

In FIG. 2b is seen probe 12 being protracted over the wire guide towards the left boundary 50 of the occlusion such that working head 14 of the probe is brought in physical contact with it. At this stage the wire guide is moved backward beyond the working head of the probe in order not to disturb operation of the probe. Upon bringing working head 14 in physical contact with the occlusion's boundary an operator pushes on pedal 22 to initiate the control unit and then high voltage pulses are generated by the control unit and sent to the working head. The emanating pulses of energy submitted from the working head towards the boundary 50 are schematically designated by reference numeral 54.

The electrical parameters for generation of pulses are set to at least partially disrupt the hard boundary, without however causing harm to the surrounding tissues.

In practice, when the probe is used for disrupting chronic coronary occlusion the energy of pulses is set in the range 0.01-0.3 Joule and the voltage in the range 3-7 kV depending on specific probe.

The number of pulses required to disrupt chronic occlusion obstructing coronary artery is 10-600.

In FIG. 2c is depicted further step of the method when the hard boundary has been crossed and the probe has been protracted further such that a depression 56 has been formed within soft core 48. At this step generation of high voltage pulses by the control unit can be stopped and no pulses are sent to working head 14. Wire guide 32 is protracted distally through the core until its distal end approaches left boundary 52.

In FIG. 2d still further step of the method is depicted. At this step the probe is protracted further until its working head 14 is brought in physical contact with the second boundary of the occlusion. Then the control unit is initiated again and pulses of energy emanate as designated by reference numeral 54 from the working head and eventually at least partially disrupt the boundary 54.

In FIG. 2e is seen the situation when the boundary 52 has been disrupted and generation of pulses by the control unit is stopped. The probe has been pushed distally such that it penetrates through occlusion 46 and probe's working head 14 is now beyond the occlusion.

In FIG. 2f is seen still next step of the method, at which the probe is retracted from the occlusion, while the wire guide is protracted along the duct 44 distally until it crosses the occlusion.

Figure 3:
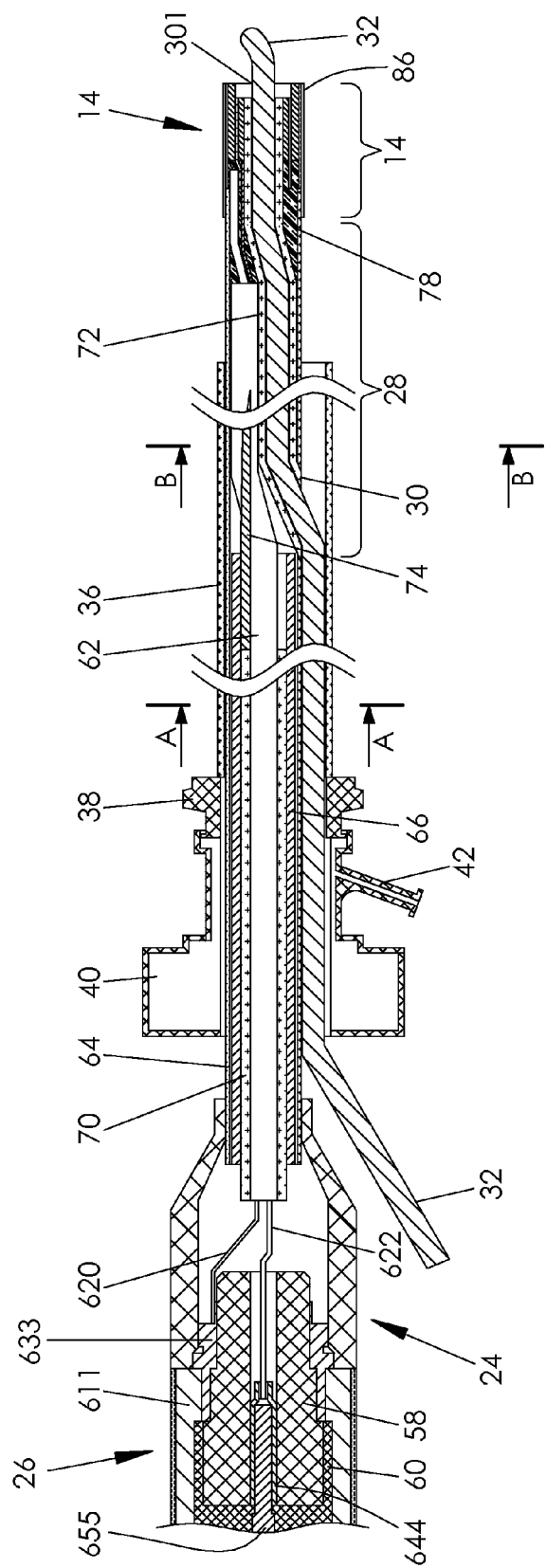
FIG. 3 illustrates an embodiment of a probe employed in the system shown in FIG. 1.

Referring now to FIG. 3 a first embodiment of the auxiliary probe employed in the system 10 will be explained.

It is seen in FIG. 3 the situation when the probe is inserted within the guiding catheter and the wire guide is introduced in the probe such that its distal end exits from the working head.

The probe's proximal end is connected to male portion 24 of the coupler and the mail portion 24 connected with the female portion 26. The male portion is fitted with a protruding insulator portion 58, having conductive regions 633 and 644. The female portion is fitted with a corresponding insulating depression 60. The female portion is fitted with a conductive bushing 611 which is electrically connected with the shield electrode (not seen) of the power cable 16. The female portion is fitted also with a conductive shaft 655 which is electrically connected with the potential electrode (not seen) of the power cable 16.

In FIG. 3 the coupler is shown in its connected state, when insulating depression 60 of the female portion receives protruding insulator portion 58 of the male portion, conductive bushing 611 of female portion is electrically connected to conductive region 633 of the male portion and conductive shaft 655 of the female portion is electrically connected to conductive region 644 of the male portion.

An inner miniature coaxial cable 62 is provided, which is located within the probe and extends from the probe's proximal end up to the working head. Electrical connection of the inner coaxial cable to the working head will be described further with reference to FIG. 4.

The inner miniature coaxial cable is fitted with a shield electrode 620 and a potential electrode 622. The inner cable's proximal end protrudes within the male portion of the coupler and potential electrode 622 passes along the insulator portion 58 and is electrically connected to conductive region 644. The shield electrode 620 is electrically connected to conductive region 633 of the insulator portion. The electrical connection can be accomplished for example by soldering, welding etc. When the coupler is in connected state the shield electrode 620 is electrically connected to the shield electrode of cable 16 while potential electrode 622 is electrically connected to the high voltage core electrode of cable 16 (not shown). By virtue of this provision there is established power line between the control unit and the probe and high voltage pulses can be transmitted from the control unit to probe's working head 14.

The probe is configured as elongate tubular member having layers and lumens inside. The probe has an outside cover 64, which is made of a polymeric material, e.g. polyimide, FEP, PTFE, Teleflex, Pebax, Teflon etc. The outside cover can be reinforced by braiding to impart certain rigidity to the probe.

Within the outside cover there extends a first lumen 66, which in this embodiment is made of stainless steel coil having inside diameter 0.6-1 mm. The first lumen begins at the probe's proximal end and has length of about 1150-1450 mm.

Within the first lumen there is received inner cable 62, being swathed by a jacket 70, having inside diameter of about 0.45 mm.

The jacket can be made for example from polyimide and can be reinforced by braiding. The jacket begins at the probe's proximal end but it is shorter than the first lumen.

It is seen also in FIG. 3 an opening 301 through which wire guide 32 can be introduced in the probe and opening 30 through which wire guide can be withdrawn from the probe. The wire guide extends along distal portion of the probe, including its working head. There is provided a second lumen 72 through which the wire guide can be displaced along the distal portion of the probe. The second lumen can be configured as a plastic tube made of polyurethane, polyimide, PTFE, Pebax, Teleflex, PEP etc.

The distal portion of the probe carries the inner cable and the wire guide received within the plastic tube (second lumen). At the same time the reminder portion of the probe carries the inner cable received in the jacket 70, which is swathed by the stainless steel coil (first lumen). By virtue of this provision the distal portion, which carries inside only the second lumen made of plastic is much more flexible than the reminder of the probe. By virtue of this provision region 28 of the probe, which lies between the working head and opening 30 has enhanced flexibility.

One should bear in mind, however, that if the flexibility is excessive it potentially might cause collapsing the probe when it should be pushed distally or turned. To provide the probe with good and reliable maneuverability a smooth transition zone is provided between relatively rigid reminder portion of the probe and much more flexible region 28. The smooth transition zone can be implemented as at least one reinforcement element 74, which is affixed to the inwardly facing surface of the outside cover 64.

Figure 6:
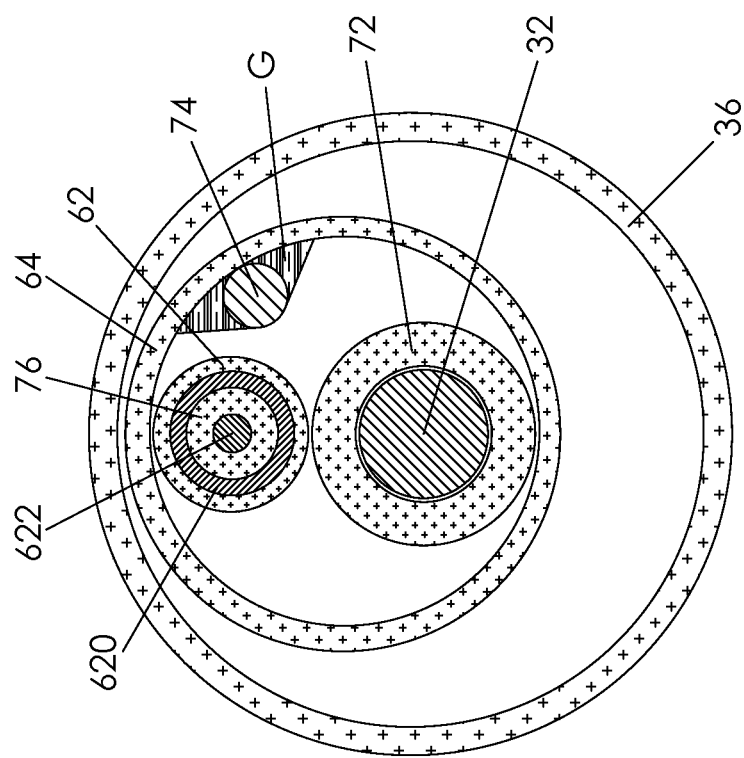
FIG. 5, FIG. 6 and FIG. 7 are respective A-A, B-B and C-C cross-sectional views of the probe seen in FIG. 3 and FIG. 4.
Figure 5:
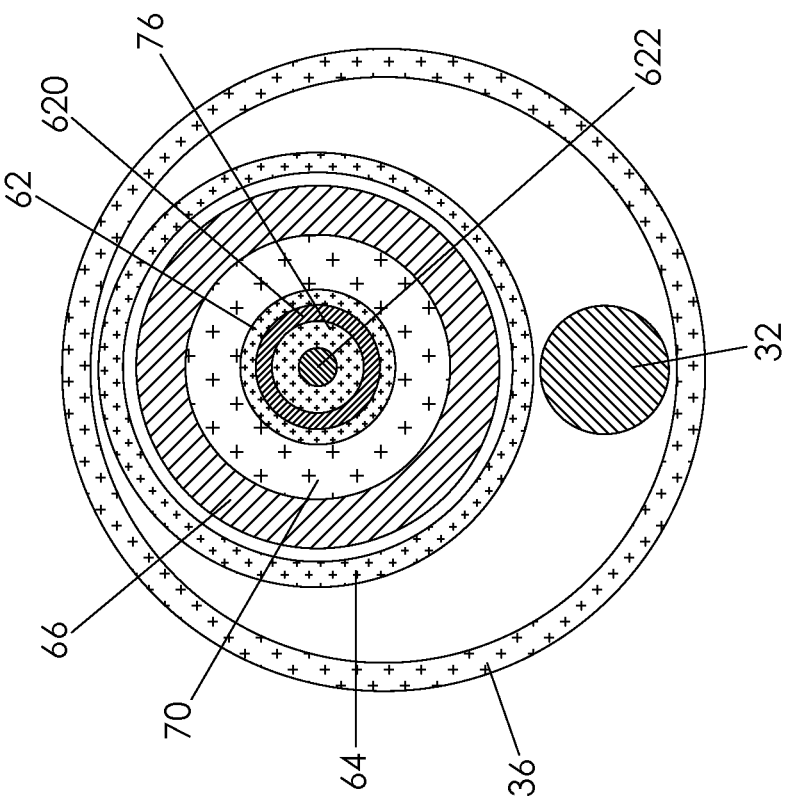
Figure 12:
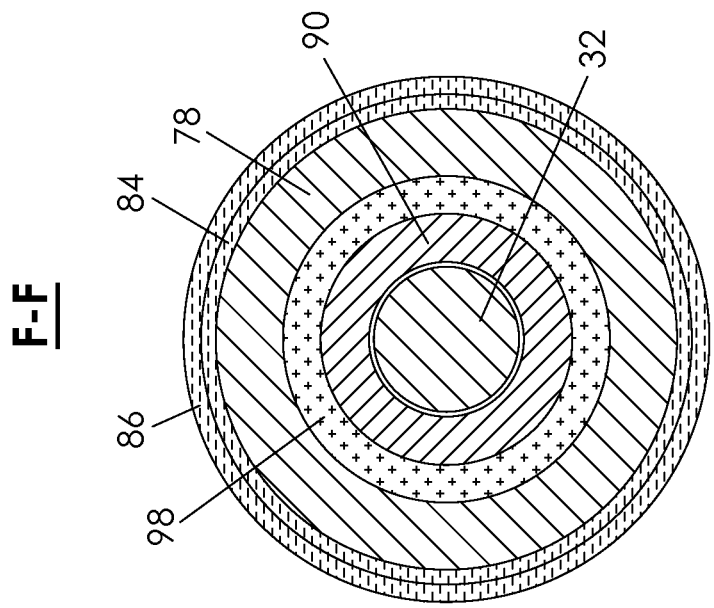
FIG. 10, FIG. 11 and FIG. 12 are respective D-D, E-E and F-F cross-sectional views of the probe seen in FIG. 8 and FIG. 9.
Figure 7:
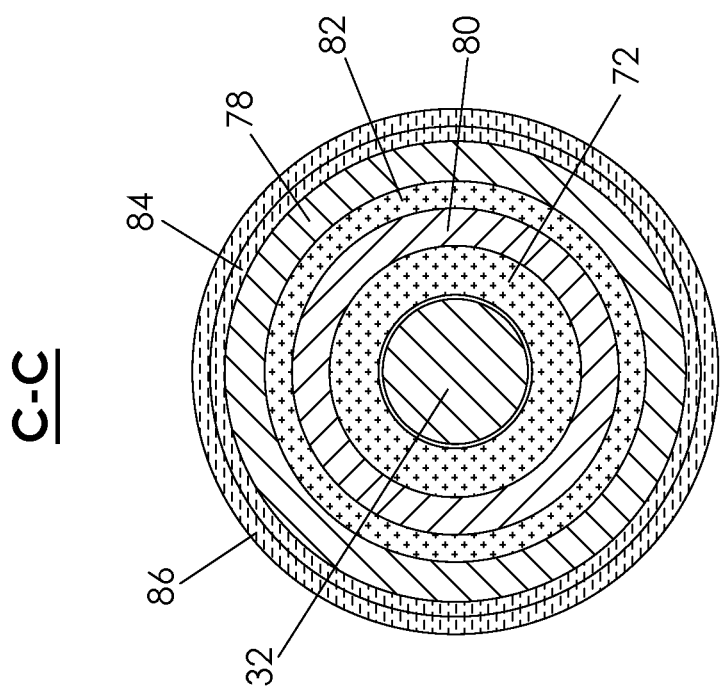

The reinforcement element is seen in FIG. 3 and in FIG. 6 being configured for example as thin metallic, e.g. stainless steel or nitinol wire having diameter 0.15-0.3 mm. The reinforcement element is affixed to the outside cover for example by a glue G. As suitable glue one can use epoxy glues or cyanoacrylates glues etc. The wire begins at a distal end of the jacket 70 and extends beyond the first lumen 66 inside distal portion of the probe. The distal end of the wire can be narrowed to impart even smoother transition to region of enhanced flexibility.

Referring now to FIGS. 4-7 construction of region 28 and adjacent thereto working head 14 will be explained.

Along the distal portion extends inner cable 62, which can be implemented as coaxial miniature microcable having electrodes 620 and 622. The electrode 622 is central potential electrode and it extends from the cable towards working head 14 being insulated by an insulation sleeve 76 made of a dielectric material, e.g. Teflon, PTFE, FEP etc. Electrode 622 can be electrically connected to outer electrode 78 by soldering, welding etc.

The electrode 620 is the shield, grounding electrode and it extends from inner cable 62 towards working head 14. Electrode 620 can be electrically connected to inner electrode 80 by soldering, welding etc.

The working head is provided with two electrodes which include an outer probe electrode 78 and an inner probe electrode 80. In practice electrodes of the working head are made from stainless steel or from Chrome containing alloy, etc. The electrodes are configured as concentric cylindrical bushings, which are electrically insulated from each other by an insulation tube 82 made from a suitable dielectric material, e.g. polyimide Teflon etc. One can readily appreciate that since the electrodes are made of metallic material it is possible to monitor the disposition of the working head within the duct. This can be accomplished for example by X-rays, ultrasound, CT or by any other physical method utilizing contrast.

Figure 4:
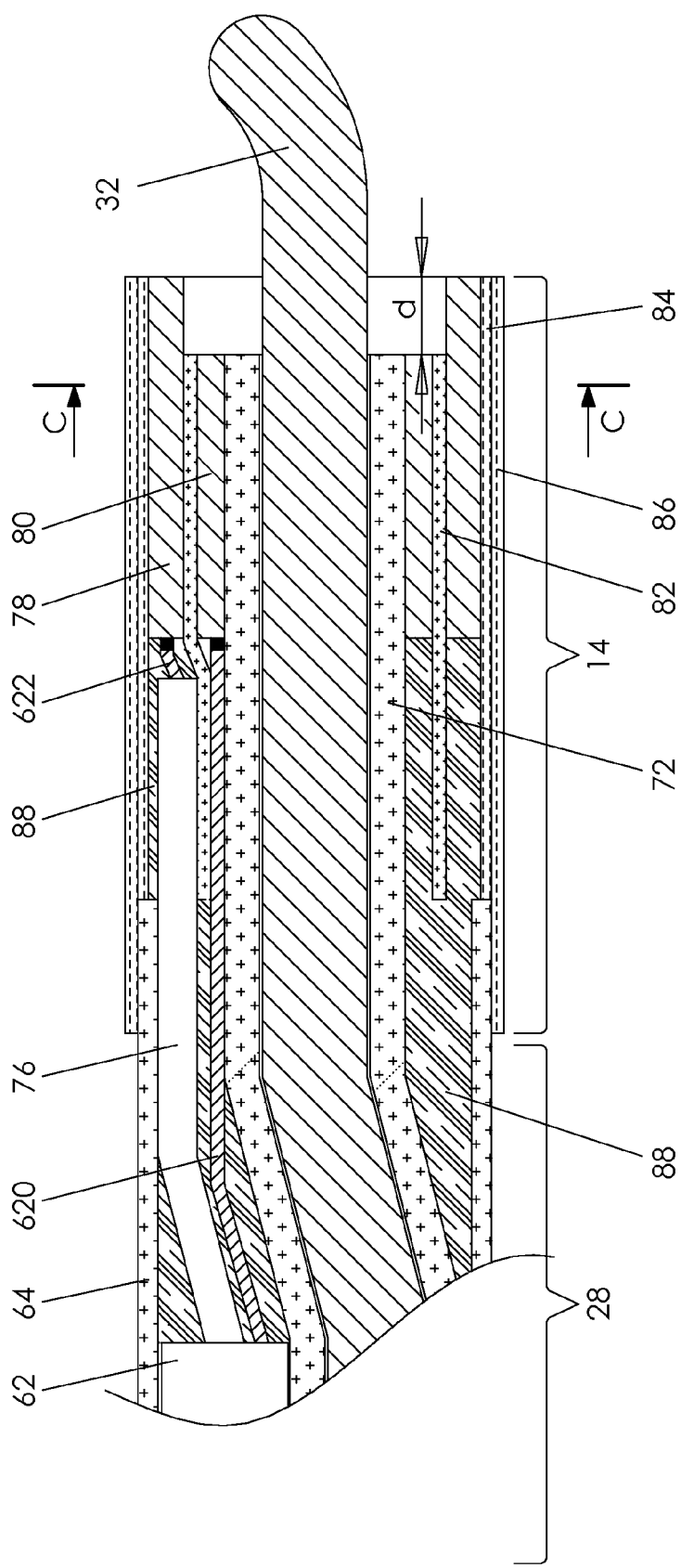
FIG. 4 depicts enlarged cross-sectional view of the distal end of the probe shown in FIG. 3.

In FIG. 4 is shown an embodiment according to which the inner electrode is buried within the working head in the sense that it is not flush with the outer electrode and there is provided a small distance d between respective distal ends of the electrodes. In practice this distance is between 0.1. and 1 mm, depending on diameter of the working head. Due to this distance the spark discharge initiated between the electrodes is located not in immediate proximity to the surrounding tissues, which renders operation of the probe less harmful to patient.

It has been empirically revealed by the inventors that the spark discharge is eventually associated with formation of shock waves which transform into acoustic waves and dissipate in the surrounding soft tissues without harming them. This renders operation of the probe even safer and less traumatic to the patient.

The shield electrode 620 of the microcable 62 is connected to proximal end of the inner electrode 80 and the central potential electrode 622 is connected to proximal end of the outer electrode 78. Connection between electrodes of microcable and electrodes of working head can be accomplished by any suitable method which ensures electrical connection and reliable transfer of high voltage pulses to the working head. In practice soldering or welding can be used.

It is seen also in FIG. 4 that wire guide 32 extends along the distal portion of the probe and its tip is outside of the working head. The wire guide is received within plastic tube 72, which electrically insulates the wire guide from the inner electrode. The wire guide's tip is shown as having radius. In practice it can be conical or flat. The wire guide can be coated by a suitable dielectric coating to reduce possibility for inducing electrical potential on the wire guide.

When electrodes of the miniature coaxial cable are connected to electrodes of the working head as described above the outer electrode 78 which is distant from the wire guide constitutes potential high voltage electrode. The inner electrode 80, which is closer to the guide wire, constitutes ground electrode. By virtue of this provision formation of electric potential on the wire guide is prevented and this renders safety to operation of the system. It should be borne in mind however that if the wire guide is coated by a dielectric coating the polarity can be reversed, i.e. the inner electrode can be potential electrode and the outer electrode can be ground electrode.

Outer electrode 78 is covered by an insulation sleeve 84 around which there is provided a cover sleeve 86. The cover sleeve is preferably made of a material which can shrink-fit around the insulation sleeve and the outside cover 64. Both the insulation sleeve and the cover sleeve are made from suitable dielectric material, e.g. polyimide, Teflon, polyurethane, polyester and have thickness of about 100 microns.

Additional electrical insulation between conducting elements of the working head is provided by filling void spaces between sleeve 76, electrodes 620, 622, lumen 72, outside cover 64 and insulation sleeve 84 by a glue 88 having dielectric properties, e.g. epoxies glues, cyanoacrylates glues etc.

Now with reference to FIGS. 8-12 another embodiment of the auxiliary probe which can be employed in the system of the present invention will be described. This embodiment differs from the previous one in that the second lumen is made form stainless steel coil instead of plastic tube. The other elements are similar to those employed in the first embodiments and therefore the similar elements are designated by the same reference numerals and are not explained in details.

A second lumen 90 is provided. The second lumen is made from stainless steel coil. The second lumen begins at lateral opening 30 and extends along region 28 of enhanced flexibility and along working head 14. The second lumen has inside diameter sufficient to allow passing the wire guide 32 such that distal end of the wire guide can be easily protracted from the working head towards the occlusion.

In this embodiment there is provided first lumen 66 which is also made from stainless steel coil. By virtue of this provision a very good flexibility and maneuverability of the distal portion is achieved. At the same time seeing that the second lumen is made of conductive material an electrical potential can be formed on the wire guide. To prevent formation of electrical potential on the wire guide there is provided an additional grounding electrode 92, which extends along the first lumen parallel to microcable 62. The additional grounding electrode is insulated from the first lumen and it has a proximal end 624 and a distal end 626. The proximal end as well as shield electrode 620 of the microcable is electrically connected to respective shield electrode of the power cable 16.

Figure 8:
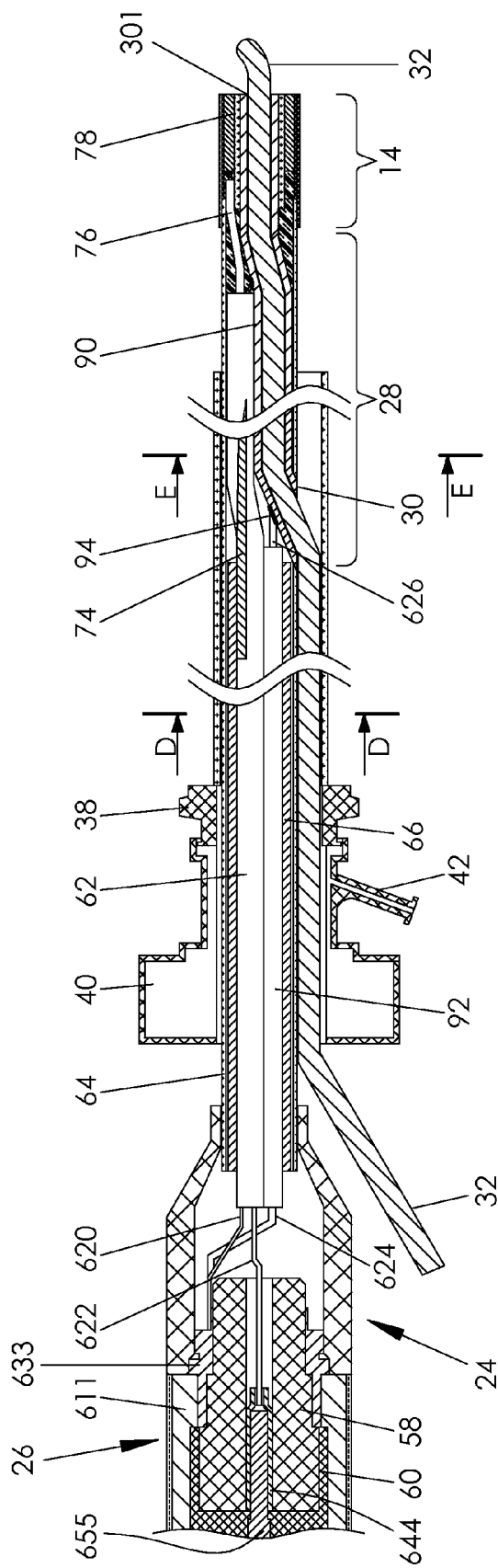
FIG. 8 is an alternative embodiment of the probe employed in the system shown in FIG. 1.

As seen in FIG. 8 distal end of the additional grounding electrode is electrically connected to second lumen 90. Connecting can be implemented e.g. by soldering, welding, etc. This is schematically designated by reference numeral 94. By virtue of the second grounding electrode it is possible to eliminate electric potential on the wire guide and thus to provide safety to the system.

Figure 9:
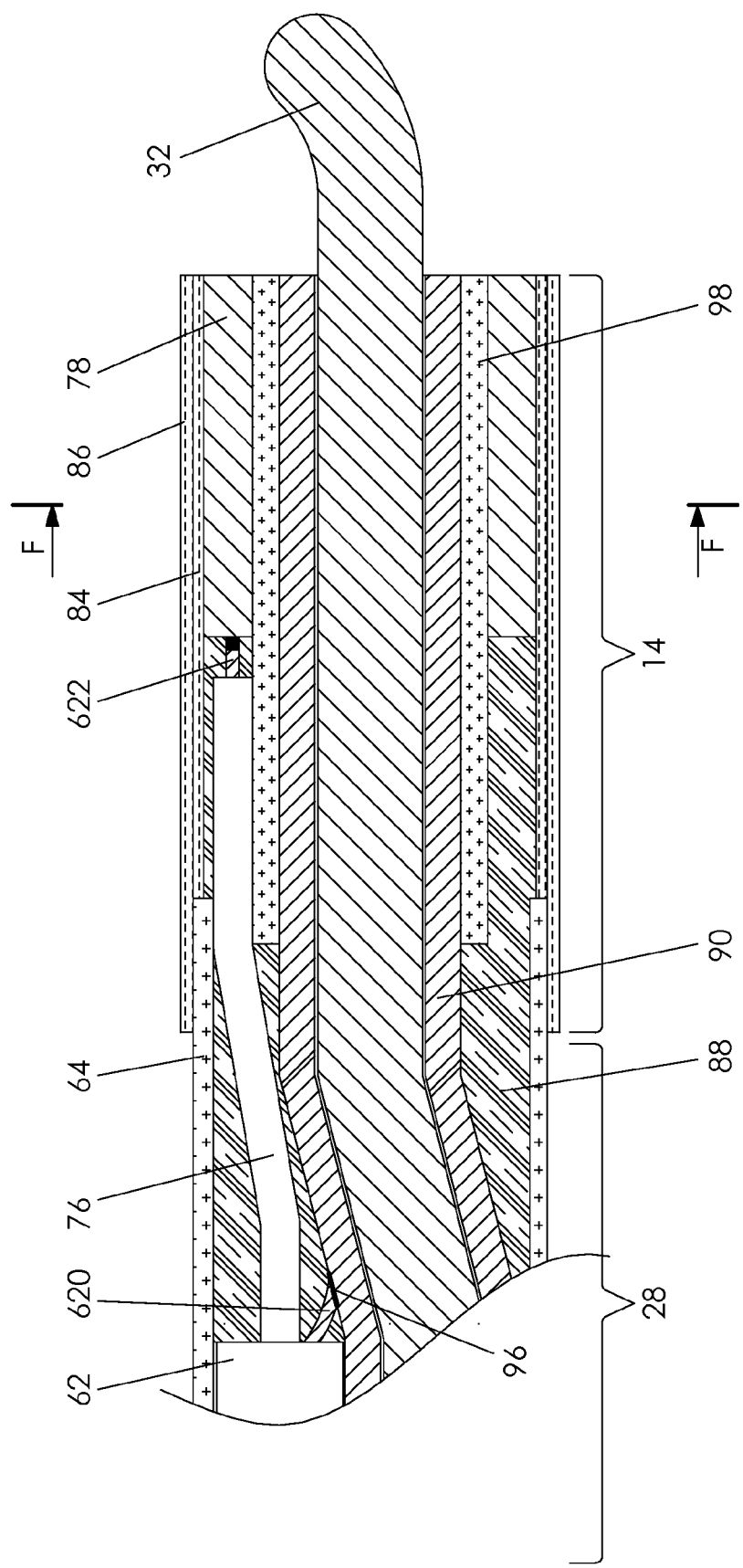
FIG. 9 is enlarged cross-sectional view of the distal end of the probe shown in FIG. 8.

Seeing that the second lumen is made of stainless steel it constitutes an inner electrode instead of cylindrical bushing 80 used in the previous embodiment. As shown in FIG. 9 shield electrode 620 is electrically connected to the second lumen, e.g. by soldering as designated by reference numeral 96.

Potential electrode 622 is electrically connected to outer electrode 78. Outer electrode 78 is electrically insulated from second lumen 90 by an insulation layer 98 made of a dielectric material like polyimide, Teflon, polyurethane etc.

As can be seen in FIGS. 8, 9 in this embodiment distal ends of both electrodes of the working head are flush.

Additional insulation between elements of the distal portion is provided by filling the void spaces with dielectric glue like epoxy or cyanoacrylates glues etc. as schematically designated by reference numeral 88.

Figure 11:
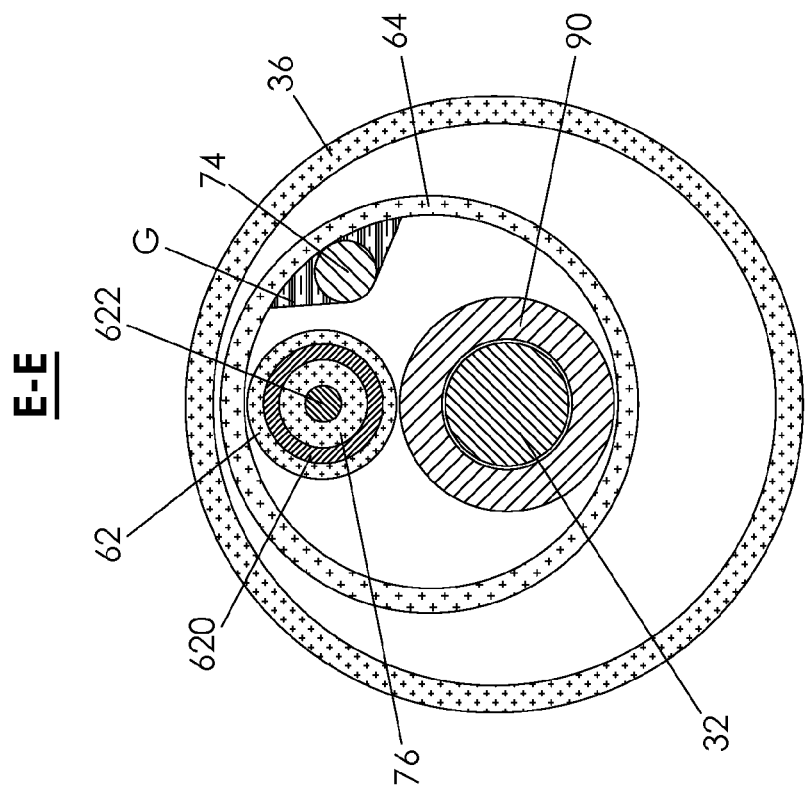
Figure 10:
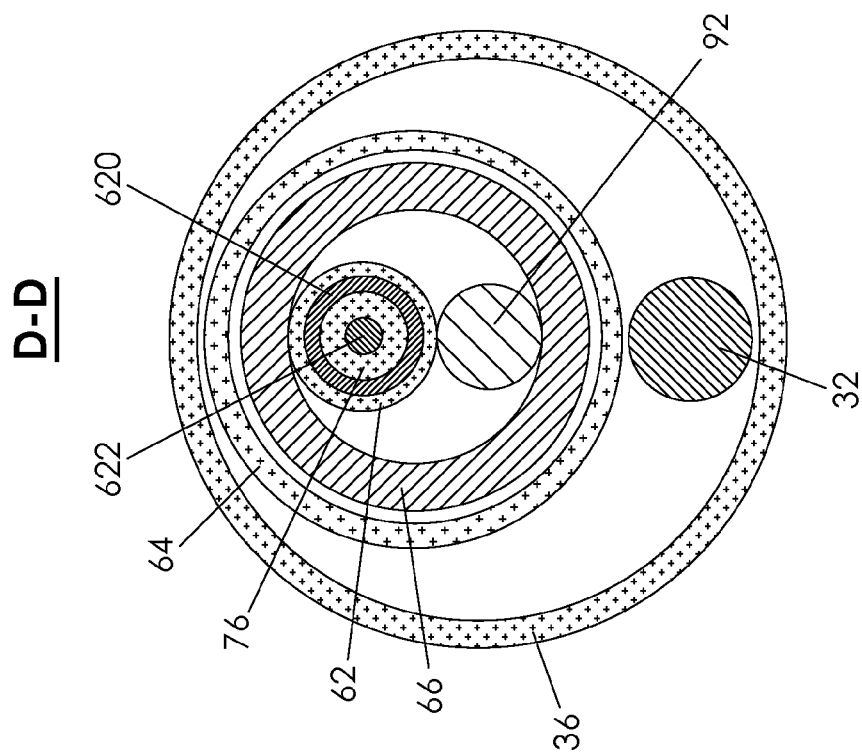

As shown in FIGS. 8 and 11 reinforcing element 74 is glued by glue G to inwardly facing surface of outside cover 64. The reinforcing element provides smooth transition zone between relatively rigid region along which extends first lumen 66 and region 28 of enhanced flexibility along which extends second lumen 90.

As shown in FIGS. 8-12 outer electrode 78 can be covered by insulation sleeve 84 and there can be provided cover sleeve 86. The cover sleeve is preferably made of a material, which can be shrink-fit around the insulation sleeve and outside cover 64.

Both the insulation sleeve and the cover sleeve can be made from suitable dielectric material, e.g. polyimide, Teflon etc. and have thickness about 100 microns.

Figure 13:
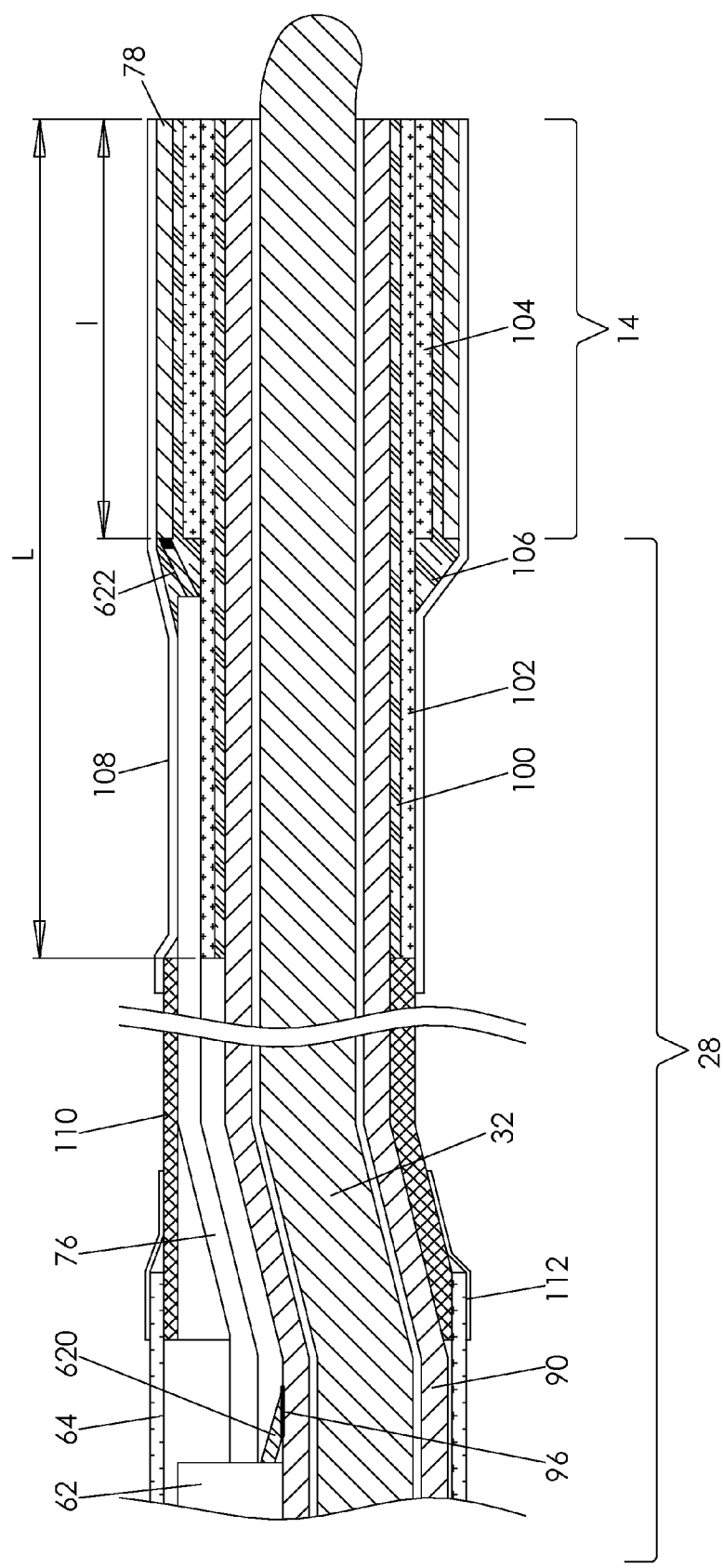
FIG. 13 is still further embodiment of the probe employed in the system shown in FIG. 1.

Now with reference to FIG. 13 still further embodiment of the auxiliary probe will be disclosed. In this embodiment the distal region is also provided with second lumen 90 configured as stainless steel coil. Wire guide 32 extends along the distal region and working head 14. The second lumen constitutes inner electrode to which shield electrode 620 of the microcable 62 is soldered or welded. Outer electrode 78 is provided, which is configured as cylindrical bushing to which potential electrode 622 is soldered or welded. Extending between second lumen 90 and outer electrode 78 several insulation layers are provided. The insulation layers comprise a first glue layer 100, a first sleeve 102, a second sleeve 104 and a second glue layer 106. The glue layers and insulation sleeves are made of a dielectric material like epoxies glues, cyanoacrylates glues etc. and polyimide, polyurethane, polyester, PTFE etc. tubes.

It is seen that length of first glue layer 100 and first sleeve 102 is L and it exceeds length of second sleeve 104 and second glue layer 106 which is I. In practice length L is about 5 mm, while length l is about 3 mm Is also seen that an external insulation sleeve 108 is provided which surrounds outer electrode 78 and the adjacent distal portion. The external insulation sleeve is made of an insulation material, e.g. polyimide, polyurethane, polyester, PTFE, FEP etc.

An intermediate coupling member 110 is provided, which covers a portion of the probe located between external insulation sleeve 108 and outside cover 64. The coupling member can be configured as a muff and it can be made of polyurethane polyester, polyimide etc. By virtue of this provision it is possible to enhance flexibility of the region 28 and at the same time to reliably electrically insulate it from the potential electrode and the shield electrode.

Proximal end of the intermediate coupling member is connected to the outside cover by a band 112, which can be made of polyimide, polyurethane, polyester, PTFE, FEP etc.

The band can be shrink-fitted over the probe and over the coupling member. Over distal end of the coupling member is shrink-fitted insulation sleeve 108. In practice the total length of the working head, the insulation sleeve and the intermediate coupling member is 15-30 mm.

Thus by virtue of the system and method of the invention it is possible to assist the wire guide to cross an occlusion in a duct of mammalian body.

It should be appreciated that the present invention is not limited to the above-described examples and that one ordinarily skilled in the art can make changes and modifications without deviation from the scope of the invention, as will be defined in the appended claims.

So for example the above-described probe could be used in a system employing electro-hydraulic principle for disrupting the occlusion.

The probe can be provided with a means for preventing bending of its distal end if the working head meets an occlusion having slanted wall. In this situation bending of the probe's distal end might reduce the disrupting efficiency. To prevent bending of the probe its distal end can be provided with a balloon arrangement, e.g. as described in US2009171278, which upon inflation centers the distal probe with respect to the duct walls.

It should also be appreciated that the features disclosed in the foregoing description, and/or in the following claims, and/or in the accompanying drawings may, both separately and in any combination thereof, be material for realizing the present invention in diverse forms thereof.

When used in the following claims, the terms "comprise", "include", "have" and their conjugates mean "including but not limited to".

The invention claimed is:

1. A system (10) for assisting a wire guide (32) to cross a duct (44) in a mammalian body when the duct is obstructed by an at least partially inorganic occlusion (46), said system being suitable to at least partially disrupt the occlusion (46) by supplying immediately to the occlusion low frequency, high voltage pulses of energy, said system comprising:
    a probe (12) insertable in the duct (44) in the mammalian body, said probe (12) having a body portion with a distal end and a proximal end, said probe (12) having a working head (14) fitted with a couple of electrodes, one of the electrodes being a potential high voltage electrode (78) and a second of the electrodes being a ground electrode (80), wherein said working head (14) is coupled to the distal end of the body portion and said probe (12) has a first lumen (66) for receiving therein a miniature coaxial cable (62);
    a control unit (18) for generation and controlling of pulses of energy supplied to the couple of electrodes (78, 80) either as discrete, one time pulses or as series of repeating pulses;
    a power cable (16) electrically connecting the probe (12) to the control unit (18), said power cable (16) suitable for supplying said pulses of energy to the potential high voltage electrode (78) and to the ground electrode (80) via the miniature coaxial cable (62) such that an electrical breakdown discharge can be provoked between the potential high voltage electrode (78) and the ground electrode (80);
    said miniature coaxial cable (62) comprising a potential electrode (622) and a shield electrode (620), said power cable (16) comprising a potential electrode and a shield electrode, wherein the potential electrode (622) of the miniature coaxial cable (62) is electrically connected to the potential electrode of the power cable (16) and the shield electrode (620) of the miniature coaxial cable (62) is electrically connected to the shield electrode of the power cable (16), in which the shield electrode (620) of the miniature coaxial cable (62) is electrically connected with the ground electrode (80) of the working head (14) and wherein the potential electrode (622) of the miniature coaxial cable (620) is electrically connected with the potential high voltage electrode (78) of the working head (14);
    wherein the probe (12) is provided with a lateral opening (30) for introducing the wire guide (32) therethrough to allow relative displacement between the wire guide (32) and the probe (12),
    and the body portion of the probe (12) comprises a region (28), which is located adjacent the working head (14), said region (28) having enhanced flexibility in comparison with a remainder of the body portion,
    wherein the first lumen (66) is longitudinally extending through the body portion except of the region (28) and said probe is provided with a second lumen (72, 90) for receiving the wire guide (32) therein, the second lumen (72) extending along the region (28) and along the working head (14), wherein said second lumen (72) being more flexible than the first lumen (66), wherein said potential high voltage electrode (78) and said ground electrode (80) is configured as a tubular body, wherein the high voltage electrode (78) is disposed concentrically with respect to the ground electrode (80) and is electrically insulated therefrom and wherein the wire guide (32) is electrically insulated from the potential high voltage electrode (78) and from the ground electrode (80).

2. A system of claim 1, in which said control unit (18) is capable generate pulses of electrical energy defined by the following parameters: frequency 1-5 Hz, duration of a single pulse not more than 5000 nanoseconds, pulse rise time less than 50 nanoseconds, pulse energy 0.01-1.0 Joule, pulse amplitude 3-15 kV.

3. A system of claim 1, comprising a coupler (C) for detachable connecting the probe (12) with the power cable (16), said coupler is provided with a male portion (24) associated with the probe (12) and with a female portion (26) associated with the power cable (16).

4. A system of claim 1, in which said power cable (16) is a high voltage coaxial cable.

5. A system of claim 1, in which the potential high voltage electrode (78) and the ground electrode (80) are configured as respective outer and inner cylindrical bushing, wherein said potential high voltage electrode (78) is coaxial with the ground electrode (80).

6. A system of claim 5, in which a distal end of the potential high voltage electrode (78) is not flush with a distal end of the ground electrode (80).

7. A system of claim 6, in which the distal end of the ground electrode (80) is buried within the working head (14) with respect to the distal end of the potential high voltage electrode (78).

8. A system of claim 1, in which the probe (12) is provided with an outside cover (64) and with at least one reinforcing element (74) such that the reinforcing element is affixed to an inwardly facing surface of the outside cover (64).

9. A system of claim 1, in which the second lumen (90) comprises a plastic tube and the first lumen (66) comprises a stainless steel coil.

10. A system of claim 1, in which the first lumen (66) and the second lumen (90) comprises a stainless steel coil.

11. A system of claim 10, in which the shield electrode (620) of the miniature coaxial cable (62) is electrically connected to the second lumen (90).

12. A system of claim 11, in which the probe (12) is provided with an additional grounding electrode (92), which is electrically connected with the shield electrode of the power cable (16) and with the second lumen (90).

13. A system of claim 12, in which the probe is provided with a coupling member (110) for coupling between the region (28) and remainder portion of the probe (12).

14. A system of claim 13, in which the coupling member (110) is configured as a muff made of a material selected from the group consisting of polyurethane, polyester and polyimide.

* * * * *